United States Patent [19]

Hawkins et al.

[11] Patent Number: 5,676,946

[45] Date of Patent: Oct. 14, 1997

[54] PHOSPHOLIPASE C HOMOLOG

[75] Inventors: Phillip R. Hawkins, Mountain View; Jeffrey J. Seilhamer, Los Altos Hills, both of Calif.

[73] Assignee: Incyte Pharmaceuticals, Inc., Palo Alto, Calif.

[21] Appl. No.: 726,883

[22] Filed: Oct. 4, 1996

Related U.S. Application Data

[62] Division of Ser. No. 419,078, Apr. 10, 1995, Pat. No. 5,587,306.

[51] Int. Cl.$^6$ .................... A61K 38/46; C12N 9/20; C12N 15/54; C12N 15/70

[52] U.S. Cl. .................... 424/94.6; 435/198; 435/252.33; 435/320.1; 435/69.1; 536/23.2

[58] Field of Search .................... 424/94.6; 435/69.1, 435/71.1, 198, 252.33, 320.1; 536/23.2

[56] References Cited

PUBLICATIONS

Ho et al., "Interluekin 4 Receptor Signaling in Human Monocytes and U937 Cells Involves the Activation of a Phosphatidylcholine–Specific Phospholipase C: A Comparison with Chemotactic Peptide, FMLP, Phospholipase D, and Sphingomyelinase", *J. Exper. Med.* (1994) 180:1457–1469.

Katz et al., "Subunits βγ of heterotrimeric G protein activate β2 isoform of phospholipase C", *Nature* (1992) 360:686–689.

Yeo et al., "Activation of Phospholipase C–γ Is Necessary for Stimulation of Phospholipase D by Platelet–derived Growth Factor", *J. Biol. Chem* (Nov. 1994) 269(45):27823–27826.

Deans et al., "Association of Tyrosine and Serine Kinases with the B Cell Surface Antigen CD20", *J. Immunol.* (Nov. 1993) 151(9):4494–4504.

Marrero et al., "Angiotensin II Stimulates Tyrosine Phosphorylation of Phospholipase C–γl in Vascular Smooth Muscle Cells", *J. Biol. Chem.* (Apr. 1994) 269:10935–10939.

Isselbacher et al., *Harrison's Principles of Internal Medicine*, McGraw–Hill, New York City (1994) 428–430.

Kuruvilla et al., "Tyrosine Phosphorylation of Phospholipase C Concomitant with its Activation by Platelet–Activating Factor in a Human B Cell Line" *J. Immun.* (1993) 151:637–648.

Rhee et al., "Regulation of Inositol Phospholipid–specific Phospholipase C Isozymes", *H. Biol. Chem.* (1992) 267:12393–12396.

*Primary Examiner*—Robert A. Wax
*Assistant Examiner*—Tekchand Saidha
*Attorney, Agent, or Firm*—Lucy J. Billings

[57] ABSTRACT

The present invention provides nucleotide and amino acid sequences that identify and encode a novel phospholipase C homolog (plch and PLCH). The present invention also provides for antisense molecules to the plch nucleotide sequences, expression vectors for the production of purified PLCH, antibodies capable of binding specifically to PLCH, hybridization probes or oligonucleotides for detecting excess PLCH-encoding nucleotide sequences, genetically engineered host cells for the expression of PLCH, diagnostic tests for activated, inflamed, diseased, and hydroxyurea-resistant cells and/or tissues based on PLCH-encoding nucleic acid molecules and antibodies capable of binding specifically to PLCH.

2 Claims, 3 Drawing Sheets

```
  1    MALLVLGLVSCTFFLAVNGLYSSSDDVIELTPSNFNREVIQSDSLMLVEFYAPWCGHCQRLTPEWKKAATALKDVVKVGAVDA
       ||-|--|||||||||||--|||||||||||--||||||||||||||||||||||||||||||||||||||||||||||||||
  1    MARLGFGLVSCTFFLAASGLYSSSDDVIELTPSNFNREVIQSNSLMLVEFYAPWCGHCQRLTPEWKKAATALKDVVKVGAVDA

84    DKHHSLGGQYGVQGFPTIKIFGSNKNRPEDYQGGRTGEAIVDAALSALRQLVKDRLGGRSGGYSSGKQGRSDSSSKKDVIELT
       |||-||||||||||||||||||||-|||||||||||||||||||||||||||||||-|||||||||||||||||||||||||
 84    DKHQSLGGQYGVQGFPTIKIFGANKNKPEDYQGGRTGEAIVDAALSALRQLVKDRLSGRSGGYSSGKQGRGDSSSKKDVIELT

167    DDSFDKNVLDSEDVWMVEFYAPWCGHCKNLEPEWAAAASEVKEQTKGKVKLAAVDATVNQVLASRYGIRGFPTIKIFQKGESP
       ||-|||||||||||||||||||||||||||||||||||-||||-|||||||||||||||||||||||-||||||||||||-|
167    DDTFDKNVLDSDDVWMVEFYAPWCGHCKNLEPEWATAATEVKEQTKGKVKLAAVDATVNQVLANRYGIRGFPTIKIFQKGEAP

250    VDYDGGRTRSDIVSRALDLFSDNAPPPELLEIINEDIAKRTCEEHQLCVVAVLPHILDTGAAGRNSYLEVLLKLADKYKKKMW
       ||||||||||||||||||||||||||||||||||||-||-||||||||||||||||||||||-  ||||||-|||||||||
250    VDYDGGRTRSDIVSRALDLFSDNAPPPELLEIINEDVAKKMCEEHQLCVVAVLPHILDTGAA..RNSYLEILLKLADKYKKKMW

333    GWLWTEAGAQSELETALGIGGFGYPAMAAINARKMKFALLKGSFSEQGINEFLRELSFGRGSTAPVGGGAFPTIVEREPCYGR
       |||||||||||||-||||||||||||||-|||||||||||||||||||||||||||||||-|||||||||-|||-----||
332    GWLWTEAGAQSELENALGIGGFGYPAMARINARKMKFALLKGSFSEQGINEFLRELSFGRASTAPVGGGSFPAITAREPWDGR

416    DGELPVEDDIDLSNVELYDLGKDEL
       |||||||||||||--|||-||-|||
415    DGELPVEDDIDLSDVELDDLEKDEL
```

FIGURE 1

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1322 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: None
        ( B ) CLONE: 9118

( x i ) SEQUENCE DESCRIPTION: SEQ ID NO:1:

```
ATGGCTCTCC  TGGTGCTCGG  TCTGGTGAGC  TGTACCTTCT  TTCTGGCAGT  GAATGGTCTG     60
TATTCCTCTA  GTGATGATGT  GATCGAATTA  ACTCCATCAA  ATTTCAACCG  AGAAGTTATT    120
CAGAGTGATA  GTTTGTGGCT  TGTAGAATTC  TATGCTCCAT  GGTGTGGTCA  CTGTCAAAGA    180
TTAACACCAG  AATGGAAGAA  AGCAGCAACT  GCATTAAAAG  ATGTTGTCAA  AGTTGGTGCA    240
GTTGATGCAG  ATAAGCATCA  TTCCCTAGGA  GGTCAGTATG  GTGTTCAGGG  ATTTCCTACC    300
ATTAAGATTT  TTGGATCCAA  CAAAAACAGA  CCAGAAGATT  ACCAAGGTGG  CAGAACTGGT    360
GAAGCCATTG  TAGATGCTGC  GCTGAGTGCT  CTGCGCCAGC  TCGTGAAGGA  TCGCCTCGGG    420
GGACGGAGCG  GAGGATACAG  TTCTGGAAAA  CAAGGCAGAA  GTGATAGTTC  AAGTAAGAAG    480
GATGTGATTG  AGCTGACAGA  CGACAGCTTT  GATAAGAATG  TTCTGGACAG  TGAAGATGTT    540
TGGATGGTTG  AGTTCTATGC  TCCTTGGTGT  GGACACTGCA  AAAACCTAGA  GCCAGAGTGG    600
GCTGCCGCAG  CTTCAGAAGT  AAAAGAGCAG  ACGAAAGGAA  AAGTGAAACT  GGCAGCTGTG    660
GATGCTACAG  TCAATCAGGT  TCTGGCCTCC  CGATACGGGA  TTAGAGGATT  CCTACAATC    720
AAGATATTTC  AGAAAGGCGA  GTCTCCTGTG  GATTATGACG  GTGGGCGGAC  AAGATCCGAC    780
ATCGTGTCCC  GGGCCCTTGA  TTTGTTTTCT  GATAACGCCC  CACCTCCTGA  GCTGCTTGAG    840
ATTATCAACG  AGGACATTGC  CAAGAGGACG  TGTGAGGAGC  ACCAGCTCTG  TGTTGTGGCT    900
GTCCTCCCCC  ATATCCTTGA  TACTGGAGCT  GCAGGCAGAA  ATTCTTATCT  GGAAGTTCTT    960
CTGAAGTTGG  CAGACAAATA  CAAAAAGAAA  ATGTGGGGGT  GGCTGTGGAC  AGAAGCTGGA   1020
GCCCAGTCTG  AACTTGAGAC  CGCGTTGGGG  ATTGGAGGGT  TTGGGTACCC  CGCCATGGCC   1080
GCCATCAATG  CACGCAAGAT  GAAATTTGCT  CTGCTAAAAG  GCTCCTTCAG  TGAGCAAGGC   1140
ATCAACGAGT  TTCTCAGGGA  GCTCTCTTTT  GGGCGTGGCT  CCACGGCACC  TGTAGGAGGC   1200
GGGGCTTTCC  CTACCATCGT  TGAGAGAGAG  CCTTGTTACG  GCAGGGATGG  CGAGCTTCCC   1260
GTGGAGGATG  ACATTGACCT  CAGTAATGTG  GAGCTTTATG  ACTTAGGGAA  AGATGAGTTG   1320
TA                                                                       1322
```

( 2 ) INFORMATION FOR SEQ ID NO:2:

( i ) SEQUENCE CHARACTERISTICS:
    ( A ) LENGTH: 566 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( A ) LIBRARY: None
    ( B ) CLONE: 9118

( x i ) SEQUENCE DESCRIPTION: SEQ ID NO:2:

```
Met Ala Leu Leu Val Leu Gly Leu Val Ser Cys Thr Phe Phe Leu Ala
 1               5                  10                  15

Val Asn Gly Leu Tyr Ser Ser Ser Asp Val Ile Glu Leu Thr Pro
            20                  25                  30

Ser Asn Phe Asn Arg Glu Val Ile Gln Ser Asp Ser Leu Trp Leu Val
        35                  40                  45

Glu Phe Tyr Ala Pro Trp Cys Gly His Cys Gln Arg Leu Thr Pro Glu
    50                  55                  60

Trp Lys Lys Ala Ala Thr Ala Leu Lys Asp Val Val Lys Val Gly Ala
65                  70                  75                  80

Val Asp Ala Asp Lys His His Ser Leu Gly Gln Tyr Gly Val Gln
                85                  90                  95

Gly Phe Pro Thr Ile Lys Ile Phe Gly Ser Asn Lys Asn Arg Pro Glu
            100                 105                 110

Asp Tyr Gln Gly Gly Arg Thr Gly Glu Ala Ile Val Asp Ala Ala Leu
        115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Ser Asp Ser Ser Ser Lys Lys
145                 150                 155                 160

Asp Val Ile Glu Leu Thr Asp Asp Ser Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ala Ser Glu Val Lys
        195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Ile Asn Glu Asp Ile Ala Lys
        275                 280                 285

Arg Thr Cys Glu Glu His Gln Leu Cys Val Val Ala Val Leu Pro His
    290                 295                 300

Ile Leu Asp Thr Gly Ala Ala Gly Arg Asn Ser Tyr Leu Glu Val Leu
305                 310                 315                 320

Leu Lys Leu Ala Asp Lys Tyr Lys Lys Met Trp Gly Trp Leu Trp
                325                 330                 335

Thr Glu Ala Gly Ala Gln Ser Glu Leu Glu Thr Ala Leu Gly Ile Gly
            340                 345                 350
```

|  | Gly | Phe | Gly<br>355 | Tyr | Pro | Ala | Met | Ala<br>360 | Ala | Ile | Asn | Ala | Arg<br>365 | Lys | Met | Lys |
|---|---|---|---|---|---|---|---|---|---|---|---|---|---|---|---|---|
|  | Phe | Ala<br>370 | Leu | Leu | Lys | Gly | Ser<br>375 | Phe | Ser | Glu | Gln | Gly<br>380 | Ile | Asn | Glu | Phe |
|  | Leu<br>385 | Arg | Glu | Leu | Ser | Phe<br>390 | Gly | Arg | Gly | Ser | Thr<br>395 | Ala | Pro | Val | Gly | Gly<br>400 |
|  | Gly | Ala | Phe | Pro | Thr<br>405 | Ile | Val | Glu | Arg | Glu<br>410 | Pro | Cys | Tyr | Gly | Arg<br>415 | Asp |
|  | Gly | Glu | Leu | Pro<br>420 | Val | Glu | Asp | Asp | Ile<br>425 | Asp | Leu | Ser | Asn | Val<br>430 | Glu | Leu |
|  | Tyr | Asp | Leu<br>435 | Gly | Lys | Asp | Glu | Leu<br>440 | Xaa | Trp | Glx | Trp | Leu<br>445 | Val | Val | Trp |
|  | Trp | Gln<br>450 | Gln | Glx | Gln | Asn | Gly<br>455 | Xaa | Trp | Val | Ala | Leu<br>460 | Val | Val | Leu | Pro |
|  | Val<br>465 | Val | Val | Val | Trp | Gln<br>470 | Ala | Val | Val | Val | Asn<br>475 | Asx | Val | Thr | Val | Ala<br>480 |
|  | Leu | Pro | Asn | Thr | Glu<br>485 | Gln | Asn | Cys | Lys | Phe<br>490 | Trp | His | His | Phe | Gly<br>495 | His |
|  | His | Asp | Arg | Asx<br>500 | His | Leu | Ala | Ser | Glu<br>505 | Arg | Trp | Arg | Ile | Thr<br>510 | Glu | Arg |
|  | Asn | Glu | Trp<br>515 | Tyr | Arg | Lys | Phe | Ala<br>520 | Ala | Pro | His | Ser | Pro<br>525 | His | Leu | Ile |
|  | Pro | Ala<br>530 | Ser | Glu | Cys | Ala | Met<br>535 | Ile | Asn | Ala | Cys | Ile<br>540 | Asp | Ser | Glu | Gln |
|  | Pro<br>545 | His | Ile | Leu | His | Ala<br>550 | Trp | Lys | Ile | Asn | Ser<br>555 | Pro | His | Ile | Leu | His<br>560 |
|  | Ala | Trp | Lys | Ile | Asn<br>565 | Ser |  |  |  |  |  |  |  |  |  |  |

( 2 ) INFORMATION FOR SEQ ID NO:3:

( i ) SEQUENCE CHARACTERISTICS:
  ( A ) LENGTH: 898 base pairs
  ( B ) TYPE: nucleic acid
  ( C ) STRANDEDNESS: single
  ( D ) TOPOLOGY: linear ( i i ) MOLECULE TYPE: cDNA ( v i i ) IMMEDIATE SOURCE:
  ( A ) LIBRARY: Human Mast Cell
  ( B ) CLONE: 9118

( x i ) SEQUENCE DESCRIPTION: SEQ ID NO:3:

```
TTCACCCGAG AAGTTATTCA GAGTGATAGT TTGTGGCTTG TAGAATTCTA TGCTCCATGG      60
TGTGGTCACT GTCAAAGATT AACACCAGAA TGGAAGAAAG CAGCAACTGC ATTAAAGAT      120
GTTGTCAAAG TTGGTGCAGT TGATGCAGAT AAGCATCATT CCCTAGGAGG TCAGTATGGT     180
GTTCAGGGAT TTCCTACCAT TAAGATTTTT GGATCCAACA AAAACAGACC AGAAGATTAC     240
CAAGGTGGCA GAACTGGTGA AGCCATTGTA GATGCTGCGC TGAGTGCTCT GCGCCAGCTC     300
GTGAAGGATC GCCTCGGGGG ACGGAGCGGA GGATACAGTT CTGGAAAACA AGGCAGAAGT     360
GATAGTTCAA GTAAGAAGGA TGTGATTGAG CTGACAGACG ACAGCTTTGA TAAGAATGTT     420
CTGGACAGTG AAGATGTTTG GATGGTTGAG TTCTATGCTC CTTGGTGTGG ACACTGCAAA     480
AACCTAGAGC CAGAGTGGGC TGCCGCAGCT TCAGAAGTAA AGAGCAGAC GAAAGGAAAA      540
GTGAAACTGG CAGCTGTGGA TGCTACAGTC AATCAGGTTC TGGCCTCCCG ATACGGGATT     600
```

| | | | | | |
|---|---|---|---|---|---|
| AGAGGATTTC | CTACAATCAA | GATATTTCAG | AAAGGCGAGT | CTCCTGTGGA | TTATGACGGT | 660 |
| GGGCGGACAA | GATCCGACAT | CGTGTCCCGG | GCCCTTGATT | TGTTTTCTGA | TAACGCCCCA | 720 |
| CCTCCTGAGC | TGCTTGAGAT | TATCAACGAG | GACATTGCCA | AGAGGACGTG | TGAGGAGCAC | 780 |
| CAGCTCTGTG | TTGTGGCTGT | CCTCCCCCAT | ATCCTTGATA | CTGGAGCTGC | AGGCAGAAAT | 840 |
| TCTTATCTGG | AAGTTCTTCT | GAAGTTGGCA | GACAAATCC | AAAAAAAAA | AAAAAAA | 898 |

( 2 ) INFORMATION FOR SEQ ID NO:4:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Hybrid T/B Lymphoblast
        ( B ) CLONE: 043866

( x i ) SEQUENCE DESCRIPTION: SEQ ID NO:4:

| | | | | | |
|---|---|---|---|---|---|
| CTGGAGCCCA | GTTGAACTTG | AGACCGCTTG | GGGATTGGAG | GGTTTGGGTA | CCCCGCCATG | 60 |
| GCCGCCATCA | ATGCACGCAA | GATGAAATTT | GCTCTGCTAA | AAGGCTCCTT | CAGTGAGCAA | 120 |
| GGCATCAACG | AGTTTTCAGG | GAGCTCTCTT | TTGGGCGTGG | CTCCACGGCA | CCTGTAGGAG | 180 |
| GCGGGGCTTT | CCCTACCATC | GTTGAGAGAG | AGCCTTGTAC | GGCAGGGATG | GCGAGCTTCC | 240 |
| CGTGGAGGAT | GACATTGACC | TCAGTGATGT | GGAGCTTGAT | GACTTAGGGA | AAGATGAAGT | 300 |

( 2 ) INFORMATION FOR SEQ ID NO:5:

( i ) SEQUENCE CHARACTERISTICS:
        ( A ) LENGTH: 170 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Corneal Stroma
        ( B ) CLONE: 046611

( x i ) SEQUENCE DESCRIPTION: SEQ ID NO:5:

| | | | | | |
|---|---|---|---|---|---|
| CATCAACGAG | TTTAGGGAG | CTCTCTTTTG | GGCGTGGCTC | CACGGCACCT | GTAGGAGGCG | 60 |
| GGCTTTCCC | TACCATCGTT | GAGAGAGAGC | CTTGTTACGG | CAGGGATGGC | GAGCTTCCCG | 120 |
| TGGAGGATGA | CATTGACCTC | AGTATGTGGA | GCTTATGAC | TTAGGGAAAG | | 170 |

( 2 ) INFORMATION FOR SEQ ID NO:6:

( i ) SEQUENCE CHARACTERISTICS:
        ( A ) LENGTH: 170 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Fibroblast
        ( B ) CLONE: 054216

( x i ) SEQUENCE DESCRIPTION: SEQ ID NO:6:

| | | | | | |
|---|---|---|---|---|---|
| CATCAACGAG | TTTAGGGAG | CTCTCTTTTG | GGCGTGGCTC | CACGGCACCT | GTAGGAGGCG | 60 |
| GGCTTTCCC | TACCATCGTT | GAGAGAGAGC | CTTGTTACGG | CAGGGATGGC | GAGCTTCCCG | 120 |

TGGAGGATGA CATTGACCTC AGTATGTGGA GCTTTATGAC TTAGGGAAAG    170

( 2 ) INFORMATION FOR SEQ ID NO:7:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Human Fetal Endothelial - Stressed
        ( B ) CLONE: 067172

( x i ) SEQUENCE DESCRIPTION: SEQ ID NO:7:

AGACAAATAC AAAAAGAAAA TGTGGGGGTG GCTGTGGACA GAAGCTGGAG CCCAGTCTGA    60

ACTTGAGACC GCTTGGGGAT TGGAGGGTTT GGGTACCCCG CCATGGCCGC CATCAATGCA    120

CGCAAGATGA AATTTGCTCT GCTAAAAGGC TCCTTCAGTG AGCAAGGCAT CAACGAGTTT    180

( 2 ) INFORMATION FOR SEQ ID NO:8:

( i ) SEQUENCE CHARACTERISTICS:
        ( A ) LENGTH: 191 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Human Fetal Endothelial - Stressed
        ( B ) CLONE: 067990

( x i ) SEQUENCE DESCRIPTION: SEQ ID NO:8:

GGGTACCCCG CCATGGCCCC ATCAATGCAC GCAAGATGAA ATTTCTCTGC TAAAAGGCTC    60

CTTCAGTGAG CAAGGCATCA ACGAGTTTTT CAGGGAGCTC TCTTTTGGGC GTGGCTCCAC    120

GGCACCTGTA GGAGGCGGGG CTTTCCCTAC CATCGTTGAG AGAGAGCCTT GTTCGGAGGG    180

ATGGCGAGCT T    191

( 2 ) INFORMATION FOR SEQ ID NO:9:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Human Fetal Endothelial - Stressed
        ( B ) CLONE: 082161

( x i ) SEQUENCE DESCRIPTION: SEQ ID NO:9:

CATGGCTCTC CTGGTGCTCG GCCTGGTGAG CTGTACCTCT TTTGGCAGTG AATGGCTGTT    60

TCCTCTAGTG ATGATGTGAT CGATTTAACT CCTCAAATTT CACCGAGAAG TTATTCAGAG    120

TGATAGTTTT GGCTTGTAGA ATTTATGCCC ATGGTGTGGT CACTGTCAAA AA    172

( 2 ) INFORMATION FOR SEQ ID NO:10:

( i ) SEQUENCE CHARACTERISTICS:
        ( A ) LENGTH: 195 base pairs
        ( B ) TYPE: nucleic acid (C) STRANDEDNESS: single
(D) TOPOLOGY: linear (i i) MOLECULE TYPE: cDNA (v i i) IMMEDIATE SOURCE:
(A) LIBRARY: Stimulated THP-1 Cells
(B) CLONE: 154746

(x i) SEQUENCE DESCRIPTION: SEQ ID NO:10:

| | | | | | |
|---|---|---|---|---|---|
| GCGGTGGGGA | CTGCACGTAG | CCCGGCGCTC | GGATGGCTCT | CCTGGTGCTC | GGTCTGGTGA | 60 |
| GCTGTACCTT | CTTTCTGGCA | GTAATGGTCT | GTATTCCTCT | AGTGATGATG | TGATCGAAAT | 120 |
| AACTCCATCA | AATTTAACCG | AGAAGTTATT | CAGAGTGATA | GTTTGTGGCT | TGTAGAATTC | 180 |
| TATGCTCCAT | GGTGT | | | | | 195 |

(2) INFORMATION FOR SEQ ID NO:11:

(i) SEQUENCE CHARACTERISTICS:
(A) LENGTH: 250 base pairs
(B) TYPE: nucleic acid
(C) STRANDEDNESS: single
(D) TOPOLOGY: linear (i i) MOLECULE TYPE: cDNA (v i i) IMMEDIATE SOURCE:
(A) LIBRARY: Stimulated THP-1 Cells
(B) CLONE: 157482

(x i) SEQUENCE DESCRIPTION: SEQ ID NO:11:

| | | | | | |
|---|---|---|---|---|---|
| GCGGCACGTG | CAAGGGCTGA | AGCGGCGGCG | GCGGTGGGGA | CTGCACGTAG | CCCGGCGCTC | 60 |
| GGCATGGCTC | TCCTGGTGCT | CGGTCTGGTG | AGCTGTACCT | TCTTTTGGCA | GTGAATGGTC | 120 |
| TGTATTCCTC | TAGTGATGAT | GTGATCGATT | AACTCCATCA | AATTTCAACC | GAGAAGTTAT | 180 |
| TCAGAGTGAT | AGTTTGTGGC | TTGTAGAATT | CTATGCTCCC | ATGGGTGTGG | TCACTGTCAA | 240 |
| AATTAACACC | | | | | | 250 |

(2) INFORMATION FOR SEQ ID NO:12:

(i) SEQUENCE CHARACTERISTICS:
(A) LENGTH: 206 base pairs
(B) TYPE: nucleic acid
(C) STRANDEDNESS: single
(D) TOPOLOGY: linear (i i) MOLECULE TYPE: cDNA (v i i) IMMEDIATE SOURCE:
(A) LIBRARY: Inflamed Adenoid
(B) CLONE: 159363

(x i) SEQUENCE DESCRIPTION: SEQ ID NO:12:

| | | | | | |
|---|---|---|---|---|---|
| GAGGGTTTGG | GTACCCGCCA | TGGCCGCCAT | CAATGCACGC | AAGATGAAAT | TTGCTCTGCT | 60 |
| AAAAGGCTCC | TTCAGTGAGC | AAGGCATCAA | CGAGTTTCTC | AGGGAGCTCT | CTTTTGGGCG | 120 |
| TGGCTCCACG | GCACCTGTAG | GAGGCGGGGC | TTTCCCTACC | ATCGTTGAGA | GAGAGCCTTG | 180 |
| GGACGGCAGG | GATGGCGAGC | TTCCGT | | | | 206 |

(2) INFORMATION FOR SEQ ID NO:13:

(i) SEQUENCE CHARACTERISTICS:
(A) LENGTH: 212 base pairs
(B) TYPE: nucleic acid
(C) STRANDEDNESS: single
(D) TOPOLOGY: linear ( i i ) MOLECULE TYPE: cDNA ( v i i ) IMMEDIATE SOURCE:
    ( A ) LIBRARY: Stomach
    ( B ) CLONE: 219512

( x i ) SEQUENCE DESCRIPTION: SEQ ID NO:13:

```
GAGGAGCACC  AGCTCTGTTT  GTGGCTGTGC  TGCCCCATTC  CTTGATACTG  GAGCTGCAGG      60

CAGAAATTCT  TATCTGGAAG  TTCTTCTGAA  GTTGGCAGCA  AATACAAAAA  GAAAATTGGG     120

GGTGGCTGTG  GACAGAAGCT  GGAGCCCAGT  CTGAACTTGA  GACCGCGTTG  GGGATTGGAG     180

GGTTTGGGTA  CCCCGCCATG  GCCGCCATCA  AT                                    212
```

PHOSPHOLIPASE C HOMOLOG

"This application is a divisional of Ser. No. 08/419,078, filed Apr. 10, 1995, now a U.S. Pat. No. 5,587,306".

FIELD OF THE INVENTION

The present invention is in the field of molecular biology; more particularly, the present invention describes the nucleic acid and amino acid sequences of a novel phospholipase C homolog derived from a mast cell library.

BACKGROUND OF THE INVENTION

Overview

Phospholipase C

Phospholipase C (PLC) belongs to a family of enzymes, also known as disulfide isomerases, which play a very important role in transmembrane signal transduction. Many extracellular signaling molecules including hormones, growth factors, neurotransmitters, and immunoglobulins bind to their respective cell surface receptors and activate PLCs. The role of an activated PLC is to catalyze the hydrolysis of phosphatidyl-inositol-4,5-bisphosphate (PIP2), a minor component of the plasma membrane to produce diacylglycerol and inositol 1,4,5-trisphosphate (IP3).

In their respective biochemical pathways, IP3 and diacylglycerol serve as second messengers and trigger a series of intracellular responses. IP3 induces the release of $Ca^{++}$ from internal cellular storage, and diacylglycerol activates protein kinase C (PKC). Both pathways are part of transmembrane signal transduction mechanisms which regulate cellular processes which include secretion, neural activity, metabolism, and proliferation. For example, interleukin 4 receptor signaling in human monocytes involves activation of PLC (Ho, JL et al. (1994) J Exper Med 180: 1457–69).

Several distinct isoforms of PLC have been identified and are categorized as PLC-beta, PLC-gamma, and PLC-delta. Subtypes are designated by adding Arabic numbers after the Greek letters, eg. PLC-beta-1. PLCs have a molecular mass of 62–68 kDa, and their amino acid sequences show two regions of significant similarity. The first region designated X has about 170 amino acids, and the second or Y region contains about 260 amino acids.

The Mechanism of G Protein-mediated Transmembrane Signaling

The activation of a particular PLC is mediated by a guanine nucleotide binding-regulatory protein (G-protein) or by the intrinsic tyrosine kinase activity of cell surface receptors. Many plasma membrane-bound receptors, including the hormone receptors, activate the cell's G proteins. Each G protein can act as a molecular switch turning on one or more membrane-bound effectors such as adenylate cyclase, ion channels, or phospholipase C.

G proteins are heterotrimers with alpha, beta, and gamma subunits. Inactive G proteins have guanine diphosphate (GDP) molecule bound tightly to their alpha subunit. When a G-protein linked receptor binds an extracellular ligand, such as a hormone, the hormone-receptor complex causes dissociation of GDP from the alpha-subunit. Immediately thereafter, GTP molecules fill the site, and activity of the alpha subunit's intrinsic ATPase causes dissociation of the G protein from the hormone-receptor complex. Simultaneously, GTP binding reduces the affinities between the alpha-, beta- and gamma-subunits and frees the beta-gamma complex. In some systems, the beta-gamma complex then activates PLC beta-2 (Katz A et al (1992) Nature 360:686–9).

Phospholipase Isoforms and Their Cellular Activity

The catalytic activities of the three isoforms of PLC are dependent upon $Ca^{++}$. It has been suggested that the binding sites for $Ca^{++}$ in the PLCs are located in the Y-region, one of two conserved regions. The hydrolysis of common inositol-containing phospholipids-phosphatidylinositol (PI), phosphatidylinositol 4-monophosphate (PIP), and phosphatidylinositol 4, 5-bisphosphate (PIP2) by any of the isoforms yields cyclic and noncyclic inositol phosphates. A large number of hormones and related molecules are known to activate phospholipases.

PLC-beta Isoforms

Both beta-1 and beta-2 isoforms of PLC are activated by certain subtypes of G-proteins and related G protein alpha-subunits during the transduction of signals from cell surface receptors to PLC. There may be two distinct types of G proteins, one pertussis toxin sensitive and the other insensitive, which activate the beta-1 isoform. Katz A et al (supra) suggest that the beta subunit of the G protein may also activate PLC beta-1. The activation of PLCs is achieved by increasing their intrinsic activity rather than by reducing the PLC's requirement of $Ca^{++}$ in the cytosol.

PLC-gamma Isoforms

The PLC gamma-1 isoform is mainly phosphorylated and activated by growth factor receptors belonging to the tyrosine kinase family. In addition, the growth factor receptors associate with the gamma-1 isoform before any tyrosine phosphorylation occurs. The major sites of tyrosine phosphorylation by the receptors for epidermal growth factor (EGF), platelet-derived growth factor (PDGF), and nerve growth factor (NGF) appear to be Tyr-771, Tyr-783, and Tyr-1254 in the PLC amino acid sequence. Phosphorylation of Tyr-783 in the gamma-1 isoform by the receptor tyrosine kinase is essential for the activation of the gamma-1 isoform.

Other evidence suggests that non-receptor protein tyrosine kinases can also phosphorylate and activate the gamma-1 isoform in response to certain cell surface receptors in leukocytes. For instance, the T cell antigen receptors complex can recognize antigens and transduce signals across the plasma membrane. Likewise, it appears that non-receptor protein tyrosine kinases can activate the gamma-2 isoform.

Evidence suggests that the activation of the gamma-2 isoform is necessary for stimulation of phospholipase D by platelet-derived growth factor (Yeo E-J et al (1994) J Biol Chem 269(45):27823–27826). Other evidence suggests that B cell surface antigen CD20 is associated with tyrosine and serine kinases and involved in tyrosine phosphorylation and activation of the gamma-1 and gamma-2 isoforms (Deans JP et al (1993) J Immunol 151 (9):4494–4504).

Growth factor-induced activation of PLCs appears to be independent of G-protein mediation. Marrero MB et al (1994, J Biol Chem 269:10935–39), however, reported an exception in rat aortic vascular smooth muscle cells where PLC-gamma-1 was activated by a G-protein-coupled receptor.

PLC-delta

Neither receptors nor transducers of the PLC-delta isoforms have been identified.

Inhibition of PLCs by Protein Kinases

Evidence suggests that the activation of protein kinases may serve as negative feed back signals and attenuate receptor-coupled PLC activity including the magnitude and duration in certain types of cells. For instance, the phosphorylation of Thr-654 in the EGF receptors by protein kinase prevents activation of the gamma-1 isoform by reducing the capacity of the receptor tyrosine kinase to phosphorylate the gamma-1 isoform. In addition, PKC activators such as cAMP and phorbol 12-myristate 13-acetate (PMA) attenuate the PIP2 hydrolysis induced by T cell antigen receptors. Likewise, the beta-1 isoform of PLC appears to be regulated by PKC in certain cells.

Effects of The Second Messengers And Calcium Cations:
Inositol trisphosphate

Once activated, PLCs catalyze the hydrolysis of phosphatidylinositol-4,5-bisphosphate (PIP2) to produce diacylglycerol and inositol 1,4,5-trisphosphate (IP3), all of which serve as second messengers. Inositol trisphosphate releases $Ca^{++}$ from intracellular stores and increases the influx of $Ca^{++}$ from the extracellular fluid. $Ca^{++}$ directly regulates target enzymes and indirectly affects other enzymes by functioning as a second messenger and interacting with $Ca^{++}$-binding proteins, such as troponin C and calmodulin.

Deactivation of the inositol trisphosphate pathway is achieved by active transport of $Ca^{++}$ into cells and extrusion of ions by plasma membrane-bound, $Ca^{++}$-pumping ATPases. Likewise, sequential phosphorylation degrades inositol trisphosphate.

Diacylglycerol

Diacylglycerol, a product of the hydrolysis by PLCs, acts as a second messenger by activating protein kinase C. After protein kinase C binds to diacylglycerol, the requirement of $Ca^{++}$ by protein kinase C decreases to the level of free $Ca^{++}$ found in the cytosol. Activated protein kinase C phosphorylates a great number of intracellular proteins. The termination of the diacylglycerol effect is achieved by enzymatic recycling to form phosphatidylinositol. Alternatively, a diacylglycerol lipase breaks down diacylglycerol.

PLC and Diseases

Evidence indicates that a high percentage of primary human mammary carcinomas concomitantly show increased levels of receptor EGF and PLC-gamma-1. Likewise, studies on spontaneous hypertensive rats have suggested that one of the main causes for the hypertension is an abnormal activation of PLC-delta-1resulting from point mutations in the X and Y regions of the PLC amino acid sequence.

The biology of PLC is reviewed, inter alia, in Isselbacher KJ et al. (1994) Harrison's Principles of Internal Medicine, McGraw-Hill, New York City; Kuruvilla A et al (1993) J Immun 151:637–648; and Rhee SG and Choi KD (1994) J Biol Chem 267:12393–12396.

SUMMARY OF THE INVENTION

The subject invention provides a unique nucleotide sequence which encodes a novel human phospholipase C homolog (PLCH). The cDNA, herein designated plch, was found primarily within Incyte Clone No. 9118 from a human mast cell cDNA library.

The invention also comprises the use of this PLCH or its variants to intercede in conditions involving physiologic or pathologic compromise which include the steps of testing a sample or an extract with plch nucleic acids, fragments or oligomers thereof. Aspects of the invention include the antisense DNA of plch; cloning or expression vectors containing plch; host cells or organisms transformed with expression vectors containing plch; a method for the production and recovery of purified PLCH from host cells; purified protein, PLCH, which can be used to generate antibodies for diagnosis or therapy of activated or inflamed cells and/or tissues; and a diagnostic test to be used on a biological sample obtained from a tumor for which hydroxyurea may be appropriate therapy.

DESCRIPTION OF THE FIGURES

FIG. 1 shows the amino acid alignment of the consensus PLCH (top lines of the pair) with MAP5PROMR, which is the Genbank designation for hamster protein disulphide isomerase/Form. I phosphoinositide-specific phospholipase family C.

DETAILED DESCRIPTION OF THE INVENTION

Definitions

Figure 2:
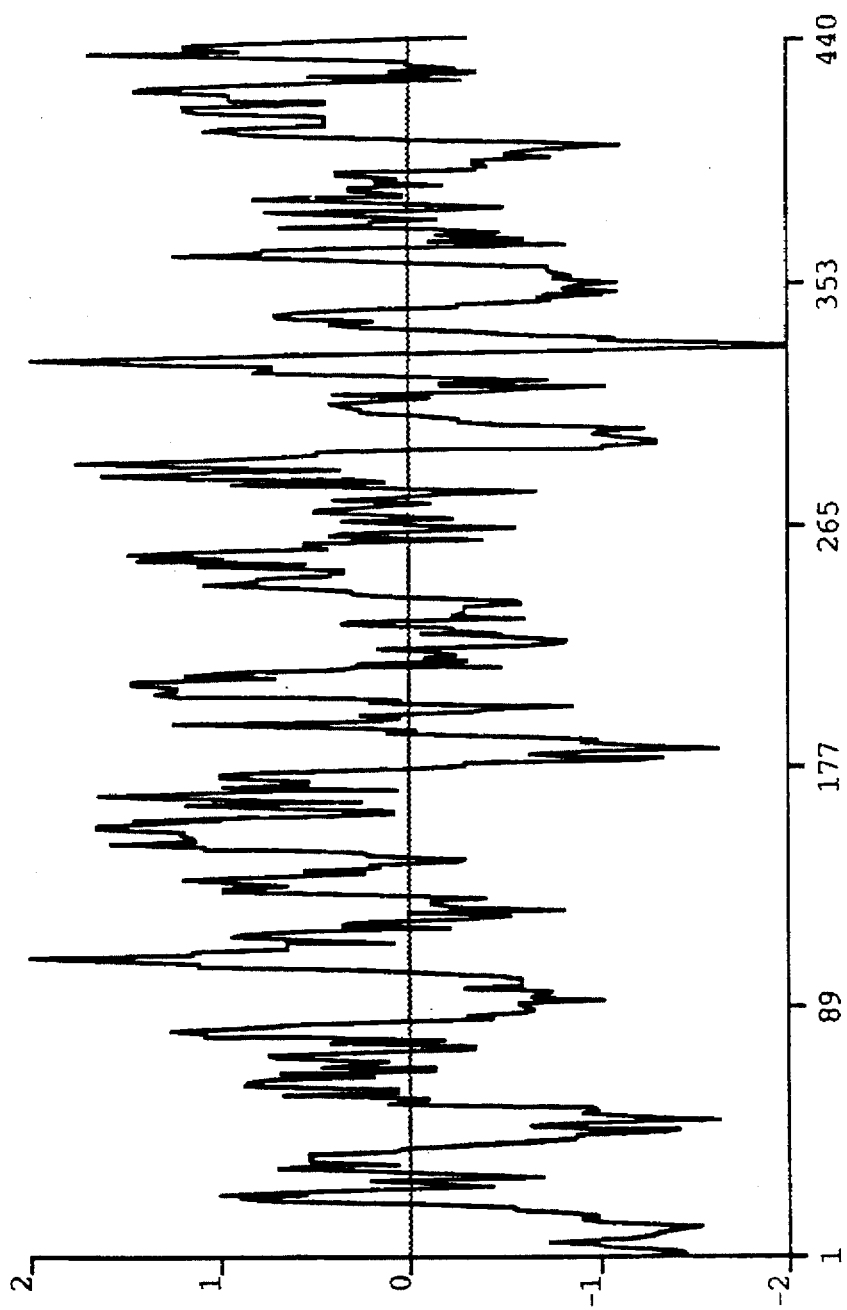
FIG. 2 displays an analysis of PLCH hydrophobicity based on the predicted amino acid sequence and composition.

As used herein, PLCH, refers to phospholipase C polypeptide homologs, naturally occurring PLCHs and active fragments thereof, which are encoded by mRNAs transcribed from the cDNA (plch) of Seq ID No 1.

"Active" refers to those forms of PLCH which retain the biologic and/or immunologic activities of any naturally occurring PLCH.

"Naturally occurring PLC" refers to PLCs produced by human cells that have not been genetically engineered and specifically contemplates various PLCs arising from post-translational modifications of the polypeptide including but not limited to acetylation, carboxylation, glycosylation, phosphorylation, lipidation and acylation.

"Derivative" refers to PLCs chemically modified by such techniques as ubiquitination, labeling (e.g., with radionuclides, various enzymes, etc.), pegylation (derivatization with polyethylene glycol), and insertion or substitution by chemical synthesis of amino acids such as ornithine, which do not normally occur in human proteins.

"Recombinant variant" refers to any polypeptide differing from naturally occurring PLCs by amino acid insertions, deletions, and substitutions, created using recombinant DNA techniques. Guidance in determining which amino acid residues may be replaced, added or deleted without abolishing activities of interest, such as normal signal transduction, may be found by comparing the sequence of the particular PLCH with that of homologous peptides and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acids. The variation allowed may be experimentally determined by systematically making insertions, deletions, or substitutions of amino acid in a PLCH molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any PLCH polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

The present invention comprises purified PLCH polypeptide from natural or recombinant sources, cells transformed with recombinant nucleic acid molecules encoding PLCH. Various methods for the isolation of PLCH polypeptide may be accomplished by procedures well known in the art. For example, such a polypeptide may be purified by immunoaffinity chromatography by employing the antibodies provided by the present invention. Various other methods of protein purification well known in the art include those described in Deutscher M (1990) Methods in Enzymology, Vol 182, Academic Press, San Diego Calif.; and in Scopes R (1982) Protein Purification: Principles and Practice, Springer-Verlag, New York City, both incorporated herein by reference.

"Recombinant" may also refer to a polynucleotide which encodes PLCH and is prepared using recombinant DNA techniques. The DNA which encodes PLCH may also include allelic or recombinant variants and mutants thereof.

"Oligonucleotides" or "nucleic acid probes" are prepared based on the cDNA sequence which encodes PLCH provided by the present invention. Oligonucleotides comprise portions of the DNA sequence having at least about 15 nucleotides, usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs encoding PLCH are present in a cell or tissue or to isolate similar nucleic acid sequences from chromosomal DNA as described by Walsh PS et al (1992 PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City, both incorporated herein by reference.

"Activated" cells as used in this application are those which are engaged in extracellular or intracellular membrane trafficking, including the export of neurosecretory or enzymatic molecules as part of a normal or disease process.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced or domains of other peptides added to modify the properties of any part of the polypeptide, to change ligand-binding affinities, interchain affinities, or degradation/turnover rate.

Detailed Description of the Invention

The present invention provides a unique nucleotide sequence identifying a novel human phospholipase C homolog which was first identified in human mast cells. The sequence first identified is shown in SEQ ID No. 3. It was found to be homologous to hamster P5 protein (Chaudhuri MM et al (1992) Biochem J 281:645–50), which itself was first identified in cell lines with increased resistance to hydroxyurea, an antineoplastic agent. Therefore, expression of PLCH is extremely useful for diagnostic purposes. Because PLCH is specifically expressed in cells active in immunity, the nucleic acid (plch), polypeptide (PLCH) and antibodies to PLCH are useful in investigations of and interventions in the normal and abnormal physiologic and pathologic processes which comprise the mast cell's role in immunity. Therefore, a diagnostic test for upregulated expression of PLCH can accelerate diagnosis and proper treatment of conditions caused by systemic and local infections, traumatic and other tissue damage, hereditary or environmental diseases associated with hypertension, carcinomas, and other physiologic/pathologic problems associated with abnormal signal transduction. In addition, because the expression of P5 protein is increased in hamster cells resistant to hydroxyurea, we propose a test for this gene for use in identifying hydroxyurea drug resistance in human neoplastic cells such as may be found in chronic granulocytic leukemia.

The nucleotide sequence encoding PLCH (or its complement) have numerous other applications in techniques known to those skilled in the art of molecular biology. These techniques include use as hybridization probes, use as oligomers for PCR, use for chromosome and gene mapping, use in the recombinant production of PLCH, and use in generation of anti-sense DNA or RNA, their chemical analogs and the like. Uses of the nucleotide encoding PLCH disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of PLCH-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring PLCH, and all such variations are to be considered as being specifically disclosed.

Although nucleotide sequences which encode PLCH and its variants are preferably capable of hybridizing to the nucleotide sequence of the naturally occurring PLCH gene under stringent conditions, it may be advantageous to produce nucleotide sequences encoding PLCH or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding PLCH and its derivatives without altering the encoded amino acid sequence include the production of RNA transcripts having more desirable properties, such as a greater half-life, than transcripts produced from the naturally occurring sequence.

The nucleotide sequence encoding PLCH may be joined to a variety of other nucleotide sequences by means of well established recombinant DNA techniques (cf Sambrook J et al. supra). Useful nucleotide sequences for joining to plch include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for plch-specific nucleic acid hybridization probes capable of hybridizing with naturally occurring nucleotide sequences encoding PLCH. Such probes may also be used for the detection of phospholipase C receptor encoding sequences and should preferably contain at least 50% of the nucleotides from this plch encoding sequence. The hybridization probes of the subject invention may be derived from the nucleotide sequence of the SEQ ID NO 1 or from genomic sequence including promoter, enhancer elements and introns of the respective naturally occurring plcs. Hybridization probes may be labeled by a variety of reporter groups, including radionuclides such as 32P or 35S, or enzymatic labels such as alkaline phosphatase coupled to the probe via avidin/biotin coupling systems, and the like.

PCR as described U.S. Pat. Nos. 4,683,195; 4,800,195; and 4,965,188 provides additional uses for oligonucleotides based upon the nucleotide sequences which encode PLCH. Such probes used in PCR may be of recombinant origin, may be chemically synthesized, or may be a mixture of both and comprise a discrete nucleotide sequence for diagnostic use or a degenerate pool of possible sequences for identification of closely related genomic sequences.

Other means of producing specific hybridization probes for plch DNAs include the cloning of nucleic acid sequences encoding PLCH or PLCH derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding PLCH and its derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the plch sequences or any portion thereof.

The nucleotide sequence can be used to construct an assay to detect activation, inflammation, or disease associated with abnormal levels of expression of PLCH. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for plch can be used to construct hybridization probes for mapping that gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of plch on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

The nucleotide sequence encoding PLCH may be used to produce purified PLCH using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. PLCH may be expressed in a variety of host cells, either prokaryotic or eukaryotic. Host cells may be from the same species in which plch nucleotide sequences are endogenous or from a different species. Advantages of producing PLCH by recombinant DNA technology include obtaining adequate amounts of the protein for purification and the availability of simplified purification procedures.

Cells transformed with DNA encoding PLCH may be cultured under conditions suitable for the expression of phospholipase C and recovery of the protein from the cell culture. PLCH produced by a recombinant cell may be secreted or may be contained intracellularly, depending on the particular genetic construction used. In general, it is more convenient to prepare recombinant proteins in secreted form. Purification steps vary with the production process and the particular protein produced.

In addition to recombinant production, fragments of PLCH may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (ABI, Foster City, Calif.) in accordance with the instructions provided by the manufacturer. Various fragments of PLCH may be chemically synthesized separately and combined using chemical methods to produce the full length molecule.

PLCH for antibody induction does not require biological activity; however, the protein must be immunogenic. Peptides used to induce specific antibodies may have an amino acid sequence consisting of at least five amino acids, preferably at least 10 amino acids. They should mimic a portion of the amino acid sequence of the protein and may contain the entire amino acid sequence of a small naturally occurring molecule like PLCH. Short stretches of PLCH amino acids may be fused with those of another protein such as keyhole limpet hemocyanin and antibody produced against the fusion protein.

Antibodies specific for PLCH may be produced by inoculation of an appropriate animal with the polypeptide or an antigenic fragment. An antibody is specific for PLCH if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse WD et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding PLCH.

An additional embodiment of the subject invention is the use of PLCH specific antibodies, receptors or the like as bioactive agents to treat systemic and local infections, traumatic and other tissue damage, hereditary or environmental diseases associated with hypertension, carcinomas, and other physiologic/pathologic problems associated with abnormal signal transduction.

Bioactive compositions comprising agonists, antagonists, or receptors of PLCH may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

The examples below are provided to illustrate the subject invention. These examples are provided by way of illustration and are not included for the purpose of limiting the invention.

EXAMPLES

I Isolation of mRNA and Construction of the cDNA Library

The majority of the consensus phospholipase C cDNA sequence was identified in clone 09118 (SEQ ID No. 3) among the sequences comprising the human mast cell library. SEQ ID Nos. 4–13 were found in the Incyte data base which has been derived from a number of different libraries. Using these sequences, one skilled in the art has sufficient information to construct full length cDNAs and use them to produce PLCH.

The cells used to prepare the human mast cell library were obtained from a Mayo Clinic cancer patient. The mast cell cDNA library was prepared by purifying poly-A$^+$ mRNA and synthesizing double stranded complementary DNA enzymatically. Synthetic adaptors were ligated to the blunt-ended cDNAs which were then ligated to the phage lambda-derived Uni-ZAP vector (Stratagene, 11099 M. Torrey Pines Rd., La Jolla, Calif. 92037). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego, Calif.) and pSHIox-1 (Novagen, Madison Wis.).

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to reinfect fresh bacterial host cells (SOLR, Stratagene), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System from QIAGEN® DNA Purification System (QIAGEN Inc, Chatsworth, Calif. 91311). This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the mast cell library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencers).

IV Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches. Alternatively, BLAST, which stands for Basic Local Alignment Search Tool, is used to search for local sequence alignments (Altschul SF (1993) J Mol Evol 36:290–300; Altschul, SF et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologes. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification, Full Length Sequencing and Translation of the Gene

Figure 3:
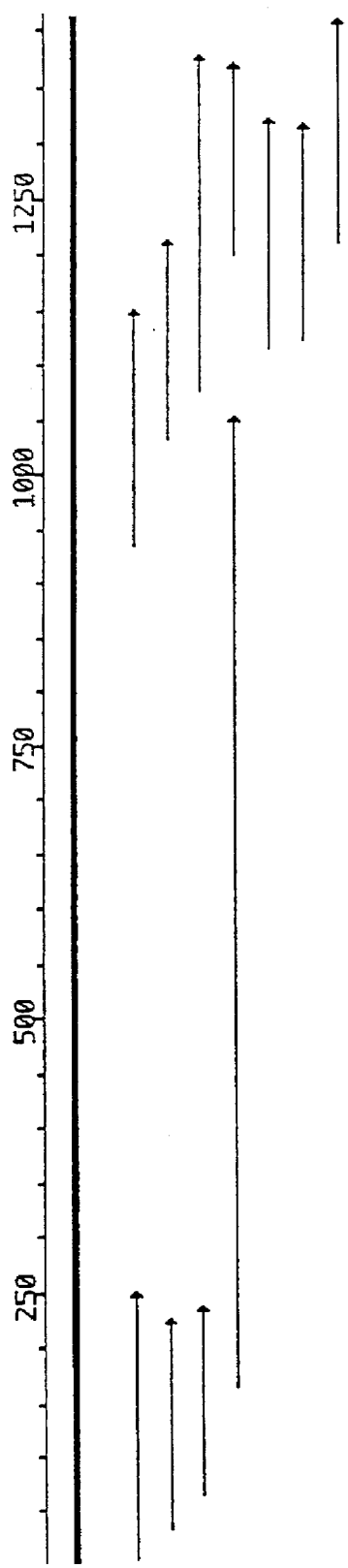
FIG. 3 a representation of the DNA sequences which were used to assemble the consensus sequence for the inventive PLCH, which is provided in SEQ ID No. 1. The DNA sequences which were assembled using the INHERIT assemblage program are given as SEQ ID Nos. 3–13.

Analysis of the INHERIT™ results from the randomly picked and sequenced portions of clones from the mast cell library identified Incyte 9118 (SEQ ID No 3) as a homolog of hamster P5 gene, or protein disulphide isomerase (Chaudhuri MM et al, supra). The cDNA insert comprising Incyte 9118 was fully sequenced using the methods described above. The insert consisted entirely of open reading frame corresponding to nucleotides numbered about 130 over 950 (data not shown). Using the insert from 9118, our database of clones (see SEQ ID Nos 4–13), the INHERIT assemblage program (ABI) and the hamster sequence as a guide, we assembled a consensus sequence which is shown as SEQ ID No 1. This sequence for human plch was translated into amino acids and is shown in Sequence ID No. 2. When the translation of the sequence was searched against protein databases such as SwissProt and PIR, no exact matches were found. FIG. 1 shows the comparison of our PLCH consensus sequence with that of the hamster P5 protein. FIG. 2 shows the hydrophobicity plot for PLCH. FIG. 3 is a representation of the assemblage of SEQ ID No 3–13.

VI Antisense analysis

Knowledge of the correct, complete cDNA sequence of PLCH will enable its use as a tool for antisense technology in the investigation of gene function. Oligonucleotides, either genomic or cDNA fragments comprising the antisense strand of plch can be used eithero in vitro or in vivo to inhibit expression of the mRNA. Such technology is now well known in the art, and probes can be designed at various locations along the nucleotide sequences. By treatment of cells or whole test animals with such antisense sequences, the gene of interest can be effectively turned off. Frequently, the function of the gene can be ascertained by observing behavior at the intracellular, cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of PLCH

Expression of plch may be accomplished by subcloning the cDNAs into appropriate expression vectors and transfecting the vectors into an appropriate expression host. In this particular case, the cloning vector previously used for the generation of the tissue library also provide for direct expression of plch sequences in *E. coil*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The plch cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced PLCH can be recovered from the conditioned medium and analyzed using chromatographic methods known in the art.

VIII Isolation of Recombinant PLCH

PLCH may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen) between the purification domain and the plch sequence may be useful to facilitate expression of PLCH.

IX Production of PLCH Specific Antibodies

Two approaches are utilized to raise antibodies to PLCH, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of PLCH, as deduced from translation of the cDNA, is analyzed to determine regions of high immunogenicity. Oligopeptides comprising appropriate hydrophilic regions, as illustrated in FIG. 2, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to o keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled PLCH to identify those fusions producing the monoclonal antibody with the desired specificity. In a typical protocol, wells of plates (FAST; Becton-Dickinson, Palo Alto, Calif.) are coated during incubation with affinity purified, specific rabbit-anti-mouse (or suitable anti-species Ig) antibodies at 10 mg/ml. The coated wells are blocked with 1% BSA, washed and incubated with supernatants from hybridomas. After washing the wells are incubated with labeled PLCH at 1 mg/ml. Supernatants with specific antibodies bind more labeled PLCH than is detectable in the background. Then clones producing specific antibodies are expanded and subjected to two cycles of cloning at limiting dilution (1 cell/3 wells). Cloned hybridomas are injected into pristane-treated mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

X Diagnostic Test Using PLCH Specific Antibodies

Particular PLCH antibodies are useful for investigation of tumor resistance to hydroxyurea, signal transduction, and the diagnosis of infectious or hereditary conditions which are characterized by differences in the amount or distribution of PLCH. Since PLCH was found in a human mast cell library, it appears to be upregulated in cell types mainly involved in immune protection or defense.

Diagnostic tests for PLCH include methods utilizing the antibody and a label to detect PLCH in human body fluids, membranes, cells, tissues or extracts of such. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850, 752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound PLCH, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on PLCH is preferred, but a competitive binding assay may be employed. These assays are described, among other places, in Maddox, Del. et al (1983, J Exp Med 158:1211).

XI Purification of Native PLCH Using Specific Antibodies

Native or recombinant PLCH can be purified by immunoaffinity chromatography using antibodies specific for PLCH. In general, an immunoaffinity column is constructed by covalently coupling the anti-PLC antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns may be utilized in the purification of PLCH by preparing a fraction from cells containing PLCH in a soluble form. This preparation may be derived by solubilization of whole cells or of a subcellular fraction obtained via differential centrifugation (with or without addition of detergent) or by other methods well known in the art. Alternatively, soluble PLCH containing a signal sequence may be secreted in useful quantity into the medium in which the cells are grown.

A soluble PLCH-containing preparation is passed over the immunoaffinity column, and the column is washed under conditions that allow the preferential absorbance of PLCH (eg, high ionic strength buffers in the presence of detergent). Then, the column is eluted under conditions that disrupt antibody/PLCH binding (e.g., a buffer of pH 2–3 or a high concentration of a chaotrope such as urea or thiocyanate ion), and PLCH is collected.

XII Drug Screening

This invention is particularly useful for screening therapeutic compounds by using PLCH or binding fragments thereof in any of a variety of drug screening techniques. The polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between PLCH and the agent being tested. Alternatively, one can examine the diminution in complex formation between PLCH and a receptor caused by the agent being tested.

Thus, the present invention provides methods of screening for drugs or any other agents which can affect signal transduction. These methods comprise contacting such an agent with PLCH polypeptide or a fragment thereof and assaying (i) for the presence of a complex between the agent and the PLCH polypeptide or fragment, or (ii) for the presence of a complex between the PLCH polypeptide or fragment and the cell, by methods well known in the art. In such competitive binding assays, the PLCH polypeptide or fragment is typically labeled. After suitable incubation, free PLCH polypeptide or fragment is separated from that present in bound form, and the amount of free or uncomplexed label is a measure of the ability of the particular agent to bind to PLCH or to interfere with the PLCH and agent complex.

Another technique for drug screening provides high throughput screening for compounds having suitable binding affinity to the PLCH polypeptides and is described in detail in European Patent Application 84/03564, published on Sept. 13, 1984, incorporated herein by reference. Briefly stated, large numbers of different small peptide test compounds are synthesized on a solid substrate, such as plastic pins or some other surface. The peptide test compounds are reacted with PLCH polypeptide and washed. Bound PLCH polypeptide is then detected by methods well known in the art. Purified PLCH can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PLCH specifically compete with a test compound for binding to PLCH polypeptides or fragments thereof. In this manner, the antibodies can be used to detect the presence of any peptide which shares one or more antigenic determinants with PLCH.

XIII Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a o polypeptide in vivo (cf. Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design efficient inhibitors. Useful examples of rational drug design may include molecules which have improved activity or stability as shown by Braxton S and Wells JA (1992 Biochemistry 31:7796–7801) or which act as inhibitors, agonists, or antagonists of native peptides as shown by Athauda SB et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id can then be used to identify and isolate peptides from banks of chemically or biologically produced peptides. The isolated peptides then act as the pharmacore.

By virtue of the present invention, sufficient amount of polypeptide may be made available to perform such analytical studies as X-ray crystallography. In addition, knowledge of the PLCH amino acid sequence provided herein will provide guidance to those employing computer modeling techniques in place of or in addition to x-ray crystallography.

XIV Identification of Other Members of the Signal Transduction Complex

The inventive purified PLCH is a research tool for identification, characterization and purification of interacting or signal transduction pathway proteins. Radioactive labels are incorporated into PLCH by various methods known in the art and used to capture either soluble or membrane-bound molecules. A preferred method involves labeling the primary amino groups in PLCH with $^{125}I$ Bolton-Hunter reagent (Bolton, AE and Hunter, WM (1973) Biochem J 133: 529). This reagent has been used to label various molecules without concomitant loss of biological activity (Hebert Calif. et al (1991) J Biol Chem 266: 18989; McColl Set al (1993) J Immunol 150:4550–4555). Membrane-bound molecules are incubated with the labeled PLCH molecules, washed to removed unbound molecules, and the PLCH complex is quantified. Data obtained using different concentrations of PLCH are used to calculate values for the number, affinity, and association of PLCH complex.

Labeled PLCH is also useful as a reagent for the purification of molecules with which PLCH interacts. In one embodiment of affinity purification, PLCH is covalently coupled to a chromatography column. Cells and their membranes are extracted, PLCH is removed and various PLCH-free subcomponents are passed over the column. Molecules bind to the column by virtue of their PLCH affinity. The PLCH-complex is recovered from the column, dissociated and the recovered molecule is subjected to N-terminal protein sequencing. This amino acid sequence is then used to identify the captured molecule or to design degenerate oligonucleotide probes for cloning its gene from an appropriate cDNA library.

In another alternate method, antibodies are raised against PLCH, specifically monoclonal antibodies. The monoclonal antibodies are screened to identify those which inhibit the binding of labeled PLCH. These monoclonal antibodies are then used in affinity purification or expression cloning of associated molecules.

Other soluble binding molecules are identified in a similar manner. Labeled PLCH is incubated with extracts or other appropriate materials derived from mast cells and putative target cells. After incubation, PLCH complexes (which are larger than the lone PLCH molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XV Use and Administration of Antibodies, Inhibitors, Receptors or Antagonists of PLCH Antibodies, inhibitors, receptors or antagonists of PLCH (or other treatments to limit signal transduction, TST), can provide different effects when administered therapeutically. TSTs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TSTs include solubility of the molecule, half-life and antigenicity/immunogenicity; these and other characteristics may aid in defining an effective carrier. Native human proteins are preferred as TSTs, but organic or synthetic molecules resulting from drug screens may be equally effective in particular situations.

TSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TST to be administered, and the pharmacokinetic profile of the particular TST. Additional factors which may be taken into account include disease state (e.g. severity) of the patient, age, weight, gender, diet, time and frequency of administration, drug combination, reaction sensitivities, and tolerance/response to therapy. Long acting TST formulations might be administered every 3 to 4 days, every week, or once every two weeks depending on half-life and clearance rate of the particular TST.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for different TSTs. Administration to cells such as nerve cells necessitates delivery in a manner different from that to other cells such as vascular endothelial cells.

It is contemplated that conditions or diseases which trigger mast cell activity may precipitate damage that is treatable with TSTs. These conditions or diseases may be specifically diagnosed by the tests discussed above, and such testing should be performed in suspected cases of systemic and local infections, traumatic and other tissue damage, hereditary or environmental diseases associated with hypertension, carcinoma, and other physiologic/pathologic problems associated with abnormal signal transduction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. A substantially purified human phospholipase C homolog comprising the amino acid sequence of SEQ ID NO:2.

2. A pharmaceutical composition comprising a substantially purified human phospholipase C homolog having the amino acid sequence of SEQ ID NO:2 in conjunction with a suitable pharmaceutical carrier.

\* \* \* \* \*